United States Patent [19]

Imperante et al.

[11] Patent Number: 5,115,049

[45] Date of Patent: May 19, 1992

[54] FATTY CARBOXYLIC SILICONE AMINE SALTS

[75] Inventors: John Imperante, Lebanon, N.J.; Anthony J. O'Lenick, Jr., Lilburn, Ga.

[73] Assignee: Siltech Inc., Norcross, Ga.

[21] Appl. No.: 656,834

[22] Filed: Feb. 19, 1991

[51] Int. Cl.$^5$ ............................................. C08F 283/00
[52] U.S. Cl. .................................. 525/479; 525/474; 528/26; 528/26.5; 528/38; 556/413; 556/419; 556/423; 556/425
[58] Field of Search ................ 528/26, 26.5, 38; 525/474, 479; 556/413, 419, 423, 425

[56] References Cited

U.S. PATENT DOCUMENTS

| 4,785,067 | 11/1988 | Brumbill | 528/26.5 |
| 4,960,845 | 10/1990 | O'Lenick, Jr. | 528/15 |
| 4,973,643 | 11/1990 | O'Lenick, Jr. | 528/15 |

Primary Examiner—Melvyn I. Marquis

[57] ABSTRACT

The invention discloses novel fatty carboxylic acid salts of organofunctional silicone amines. The amino pendant functionality is present within the polymer. Compounds of the invention by virtue of their being salts, deposit on the surface of various substrates. Thereby altering the substrate's surface physical properties. The desirable durable properties which can be given to substrates include; softness, lubrication, soil release, and hydrophobicity. The compounds of the present invention are prepared by the neutralization of a silicone amine with a fatty carboxylic acid.

10 Claims, No Drawings

FATTY CARBOXYLIC SILICONE AMINE SALTS

BACKGROUND OF THE INVENTION

1. Field of Invention

The invention discloses novel fatty carboxylic acid salts of organofunctional silicone amines and applications of these materials. The amino pendant functionality is present within the polymer. Compounds of the invention by virtue of their being salts, have better solubility in many organic systems and deposit on the surface of various substrates. Thereby altering the substrate's surface physical properties. The desirable durable properties which can be given to substrates include; softness, lubrication, soil release, and hydrophobicity. The compounds of the present invention are prepared by the neutralization of a silicone amine with a fatty carboxylic acid.

2. Description of the Arts and Practices

Silicone compounds have been known to be active at the surface of hair, plastic, cellulosic and synthetic fibers as well as paper. They are good nondurable lubricants and are very stable to oxidation, however, their high cost and lack of efficiency at low concentrations as well as low durability have made their acceptance in commercial products quite low. In all instances, commercially available quats are the active ingredient in traditional laundry care markets, with little or no silicone added.

The low efficiency and low durability of dimethylpolysiloxane is due to the fact that it is very water insoluble and deposits on the surface to obtain a minimum free energy in the solution. Simply, the silicone oil delivery is to the surface by hydrophobic binding, not chemical bonding. At the surface, the dimethylpolysiloxane is a very effective fiber lubricant, however, there are two drawbacks, first; the dimethylpolysiloxane is not chemically bonded so the effect is very transient and disappears with one washing, and second; since there is no reaction of the dimethylpolysiloxane to the surface an equilibrium between fiber absorbed dimethylpolysiloxane and dimethylpolysiloxane in the dispersion results in very inefficient percentage of silicone deposited. A large amount of the expensive silicone goes down the drain with the waste water.

One major problem which is encountered formulating with silicone compounds is the selection of solvents in which the silicone oil is placed. Silicone oils are insoluble in mineral oil, water, most protic solvents and many other solvents. Most are soluble in mineral spirits which is volatile and limits the ability to formulate personal care products. Many attempts have been made to formulate silicone products which are useful in a variety of solvents.

Many attempts have been made to overcome these problems and get a truly substantive product, which deposits efficiently. One approach has been to use hydrosilation technology to make alkoxylated silicone polymers, used as raw materials in this invention. These materials do not have the substantivity desired to make them suitable for use as antistats, softeners and or soil release agents. Hydrosilation technology is known to those skilled in the art and is outlined in U.S. Pat. No. 4,083,856. These materials, prepared by the hydrosilation of a vinyl alkoxylated alcohol and a silanic hydrogen containing polymer, by virtue of their alkoxylation, exhibit a high cloud point classically seen in nonionics, which is a point were at some elevated temperature, the silicone polymer comes out of solution and becomes more substantive to the hydrophobic substrate. This approach allows for better efficiencies but does little if anything for long term substantivity.

U.S. Pat. No. 3,511,699 to Sterman issued May 12, 1970 teaches that epoxy compounds placed in the silicone backbone by hydrosilation can be cured onto certain fibers to give improved substantivity. The substantivity is based upon the reaction of hydroxyl groups on the cellulosic and the epoxy group in the silicone polymer. The resulting bond is a ether linkage and a new hydroxyl group. While a definite improvement over earlier compounds the efficiency and durability of these compounds are not enough to allow for cost effective incorporation of these materials in detergent formulations.

U.S. Pat. No. 4,960,845 to O'Lenick issued October 1990 discloses sulfated silicone polymers which are high foaming surfactants.

U.S. Pat. No. 4,973,643 to O'Lenick issued November 1990 discloses ether amine compounds useful as raw materials in the preparation of the compounds of the present invention.

U.S. Pat. No. 3,801,572 to Berger issued April 1974 discloses amino silicones suitable as raw materials in the present invention.

One attempt to provide silicone amines which are soluble in organic oils was to mix the amine into a fatty alcohol. This attempt failed resulting in separation. We surprisingly found that when the amine is neutralized with a fatty acid a stable waxy solid results. This wax has solubility in mineral and other oils. By proper selection of the silicone amine and of the fatty acid products having varied solubility can be prepared. Product hardness can also be varied by the proper selection of raw materials.

Object of the Invention

It is the object of the present invention to provide novel fatty carboxylic salt of an amino functional silicone polymer compounds. The products have unique solubilities in organic oils and are surface active analogues of soap. They are substantive to the surface of a fibrous, plastic or cellulosic material, which results in softness, lubricity, and hydrophobicity.

It is another objective of the current invention to provide fatty carboxylic acid salts of amino silicone polymers which can be used in textile and laundry applications to render antistatic, softness and lubrication properties to the fibers and consequently the garments treated. The superior antistatic properties are an important benefit, since this is a major aspect of consumer perception of softness in consumer and industrial laundry applications. Lubrication has been a property which is purported to effect garment life. These salts are also uniquely suited for use in personal care products like shampoos as a conditioner.

Summary of the Invention

The present invention relates to novel fatty carboxylic acid salts of amino silicone polymer compounds. The polymers by virtue of the fact that they are fatty carboxylic salts deposit on substrate surfaces and form effective surface modifying finishes. The compounds of the present invention are substantive to cellulosic and synthetic fibers as well as metal surfaces and plastic polymers.

The compounds of this invention conform to the following formula;

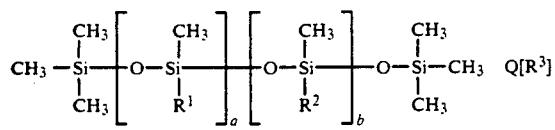

a is an interger from 1 to 200;
b is an interger from 1 to 50;
$R^1$ is selected from —$CH_3$ and phenyl;
$R^2$ is selected from;
- —$(CH_2)_3$—$(OCH_2CH_2)_x$—$(OCH_2CH(CH_3))_y$—$(OCH_2CH_2)_z$—$NH_3$;
- —$(CH_2)_3$—$(CH_2)_w$—$NH_3$; and
- —$(CH_2)_3$—$(CH_2)_v$—$N(H)_2$—$[(CH_2)_3$—$N(H)_2]_m$—H;

x, y and z are integers and are independently selected from 0 to 20;
w is an integer ranging from 0 to 5;
v is an integer ranging from 0 to 5;
m is an integer from 1 to 10.
$R^3$ is the anion of a fatty carboxylic acid and conforms to the following structure;

$R^4$ is alkyl having from 5 to 45 carbon atoms or mixtures thereof;
Q is an integer needed for charge balance and is equal to the number of nitrogen atoms present in the $R^2$ group.

The products of the present invention are prepared by neutralization of a the above specified silicone amines with an equivalent of a fatty carboxylic acid. This means that for each nitrogen atom present in the silicone pendant group there will be present one carboxylic acid anion.

The salts of the primary amines have the amino group present at the terminal part of the pendant group and conform to the following structure;

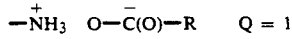

In the case were there is a diamine there will be a need for two equivalents of carboxylic acid to neutralize the amines.

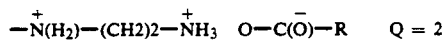

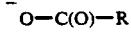

It is clear therefore that the value of Q will equal the number of amine groups present in the silicone compound.

PREFERRED EMBODIMENT

In a preferred embodiment the number of carbon atoms in the fatty carboxylic acid ranges from 12 to 22. This results in a waxy paste which liquefies under pressure, and is excellent as a hair and skin conditioner and softener.

In another preferred embodiment the amines used for the neutralization are ether amines disclosed in U.S. Pat. No. 4,973,643 to O'Lenick. These amines are items of commerce marketed under the Silube trade name and available from Siltech Inc. Norcross Ga.

In another embodiment the molar ratio of amine to acid is between 0.5:1 to 1:0.5. In the case where there is an excess of amine, the pH of the dispersion will be alkaline. The pH will be acidic when there is an excess of acid. When equimolar amounts are used the pH will be neutral. One preferred embodiment is when a 1:1 mole ratio is used, giving a neutral product. Another preferred embodiment is when there is an excess of acid resulting in a pH of about 5. This pH is close to the pH of skin and therefore is the desired pH for skin care products.

In still another preferred embodiment the compounds of the present invention are applied in an effective conditioning concentration to fiber. These fibers can be synthetic or natural. A most preferred fiber is hair and the compound can be applied either in a shampoo or in a conditioning product. The effective conditioning concentration ranges from 0.001 to 25%, but the preferable concentration ranges from 0.1 to 5%.

RAW MATERIAL EXAMPLES

Fatty Acids

Fatty acids which are suitable for the preparation of compounds of the present invention include the following fatty acids and mixtures thereof. The compounds conform to the following structure;

| | R—C(O)—OH | |
|---|---|---|
| Name | R | Double Bonds |
| Caproic | $C_5H_{12}$ | 0 |
| Caprylic | $C_7H_{16}$ | 0 |
| Carpic | $C_9H_{20}$ | 0 |
| Lauric | $C_{11}H_{34}$ | 0 |
| Myristic | $C_{13}H_{28}$ | 0 |
| Palmitic | $C_{15}H_{32}$ | 0 |
| Stearic | $C_{17}H_{36}$ | 0 |
| Arachic | $C_{19}H_{40}$ | 0 |
| Hydroxy Stearic | $C_{17}H_{36}O$ | 0 |
| Behenic | $C_{21}H_{44}$ | 0 |
| Lignoceric | $C_{24}H_{48}$ | 0 |
| Oleic | $C_{17}H_{34}$ | 1 |
| Erucic | $C_{21}H_{42}$ | 1 |
| Linoleic | $C_{17}H_{32}$ | 2 |
| Linolenic | $C_{17}H_{30}$ | 3 |
| Tetracosenic | $C_{24}H_{40}$ | 5 |
| Unicid ™ 700 | $C_{46}H_{92}$ | 0 |

Unicid ™ is a trademark of Petrolite Specialty Polymers Group, Tulsa OK.

It is clearly understood to those skilled in the art that there are many oils such as coconut fatty acid, soybean fatty acid and many others which are suitable for preparation of the compounds of the present invention.

It should also be understood that the oil can be used for the preparation of the fatty carboxylic salt by mixing the amine and the oil using the process specified. The oil is thereby saponified. The by product glycerine either is left in the product or it becomes insoluble, separates from the product where it is removed.

Silicone Amines

The raw materials useful in the preparation of the compounds of the present invention can be divided into three classes depending upon the R2 group. All compounds have the following generic structure;

$$CH_3-\underset{\underset{CH_3}{|}}{\overset{\overset{CH_3}{|}}{Si}}-\left[O-\underset{\underset{R^1}{|}}{\overset{\overset{CH_3}{|}}{Si}}\right]_a-\left[O-\underset{\underset{R^2}{|}}{\overset{\overset{CH_3}{|}}{Si}}\right]_b-O-\underset{\underset{CH_3}{|}}{\overset{\overset{CH_3}{|}}{Si}}-CH_3$$

Class 1
$R^2$ is $-(CH_2)_3-(OCH_2CH_2)_x-(OCH_2CH(CH_3))_y-(OCH_2CH_2)_z-NH_2$:

| Example | $R^1$ | a | b | x | y | z |
|---|---|---|---|---|---|---|
| 1 | Methyl | 46 | 1 | 0 | 0 | 0 |
| 2 | Methyl | 150 | 4 | 5 | 5 | 5 |
| 3 | Methyl | 100 | 2 | 0 | 10 | 5 |
| 4 | Phenyl | 200 | 10 | 0 | 0 | 0 |
| 5 | Methyl | 20 | 20 | 0 | 0 | 0 |
| 6 | Ethyl | 50 | 1 | 20 | 20 | 20 |

Class 2
$R^2$ is $-(CH_2)_3-(CH_2)_w-NH_2$:

| Example | $R^1$ | a | b | w |
|---|---|---|---|---|
| 7 | Methyl | 100 | 2 | 0 |
| 8 | Methyl | 200 | 1 | 0 |
| 9 | Methyl | 50 | 3 | 1 |
| 10 | Phenyl | 50 | 4 | 0 |
| 11 | Methyl | 25 | 1 | 0 |
| 12 | Methyl | 100 | 5 | 4 |

Class 3
$R^2$ is $-(CH_2)_3-(CH_2)_w-N(H)-[(CH_2)_3-N(H)]_m-H$:

| Example | $R^1$ | a | b | w | m |
|---|---|---|---|---|---|
| 13 | Methyl | 100 | 4 | 0 | 0 |
| 14 | Methyl | 50 | 5 | 1 | 0 |
| 15 | Phenyl | 75 | 1 | 0 | 0 |
| 16 | Methyl | 175 | 10 | 0 | 1 |
| 17 | Methyl | 125 | 1 | 0 | 0 |
| 18 | Methyl | 200 | 10 | 4 | 1 |
| 19 | Phenyl | 50 | 1 | 5 | 0 |
| 20 | Methyl | 50 | 10 | 0 | 5 |

NEUTRALIZATION REACTIONS

General Procedure

The compounds of the present invention are prepared by the neutralization of the silicone amine by an equivalent amount of the fatty acid specified. The amine and fatty acid are added together and heated generally to between 100° and 140° C. until a clear homogeneous liquid is obtained. The reaction mass is then cooled to provide the desired product which is used without subsequent purification.

EXAMPLE 21

To a suitable mixing vessel with agitation and nitrogen sparge is added 282.0 grams of stearic acid, and 3,566.0 grams of Silicone amine Example 1. The reaction mass is heated to 120° C. under agitation with a small amount of nitrogen being bubbled through the reaction mixture. The reaction mass clears and is allowed to cool. The product is used without additional purification.

EXAMPLE 22-41

Example 21 is repeated only this time substituting the specified amount of the specified amine for the silicone amine example 1 and the specified amount of the specified fatty acid for the stearic acid used in example 21.

| | Silicone Amine | Fatty Acid | |
|---|---|---|---|
| Example | Example #/Grams | Type | Grams |
| 22 | 1 3,566.0 | Caproic | 116.0 |
| 23 | 2 3,667.0 | Caprylic | 144.0 |
| 24 | 3 4,708.0 | Capric | 172.0 |
| 25 | 4 2,797.0 | Lauric | 200.0 |
| 26 | 5 200.0 | Myristic | 228.0 |
| 27 | 6 9,800.0 | Palmitic | 256.0 |
| 28 | 7 3,804.0 | Stearic | 284.0 |
| 29 | 8 14,976.0 | Arachic | 312.0 |
| 30 | 9 1,306.0 | Hydroxy Stearic | 300.0 |
| 31 | 10 979.5 | Behenic | 340.0 |
| 32 | 11 2,054.0 | Lignoceric | 368.0 |
| 33 | 12 1,806.4 | Oleic | 282.0 |
| 34 | 13 2,000.0 | Erucic | 338.0 |
| 35 | 14 1,091.8 | Linoleic | 280.0 |
| 36 | 15 5,813.0 | Linolenic | 278.0 |
| 37 | 16 1,412.0 | Tetracosenic | 358.0 |
| 38 | 17 9,513.0 | Unicid 700 | 701.0 |
| 39 | 18 1,500.0 | Palmitic | 256.0 |
| 40 | 19 3,901.0 | Stearic | 284.0 |
| 41 | 20 974.0 | Arachic | 312.0 |

APPLICATIONS EVALUATION

Textile Softening

A 1% dispersion of the tested compounds were applied to white cotton fabric using AATCC Test Method 117-1979. The softness as well as the color fastness was tested. Softness was tested by hand and was rated on a 1-5 basis. (1 being the most soft, 5 being the least soft).

| Compound | CAS Number | Yellowness |
|---|---|---|
| Stearyl Alkonium Chloride | 68122-86-1 | 5 |
| Tallow Amido Quat | 61789-81-9 | 4 |
| Tallow Imidazoline Quat | 65098-88-6 | 4 |
| Compounds of this invention | | |
| Example 27 | | 2 |
| Example 34 | | 2 |
| Example 30 | | 1 |

Color Fastness

Color fastness was tested using a heat test that applies a 400° F. (205° F.) hot iron to the treated fabrics for 180 seconds. The color of the fabric is then rated on a 1-5 basis for yellowness, (5 being the most yellow).

| Compound | CAS Number | Yellowness |
|---|---|---|
| Stearyl Alkonium Chloride | 68122-86-1 | 4 |
| Tallow Amido Quat | 61789-81-9 | 4 |
| Tallow Imidazoline Quat | 65098-88-6 | 5 |
| Example 27 | | 2 |
| Example 34 | | 2 |
| Example 30 | | 1 |

Shampoo Formulation

Wet Comb Out Test

A laboratory test is conducted to screen the wet comb properties of a representative member of the family of novel compounds. Hair swatches are purchased from a supply of human hair from the same head. Each test swatch contains 7 grams of hair and is 11 inches in length. The hair is tied tightly 1 inch from one end with string. The swatch is pre-cleaned with a 3% solution of ammonium lauryl sulfate. Subsequently, the swatch is washed under running tap water. The hair is then squeezed out and while still damp dipped into a 200 ml solution of 0.2% active quaternary. Another rinse is made, then the swatch is blotted dry. The swatch is then treated by holding the hair swatch, combing the hair as rapidly as possible while alternating the side of the swatch combed. The time needed to get one smooth free stroke without tangling is recorded. Typical results for the standard quaternary compounds used in hair conditioning (stearyldimethylbenzyl ammonium chloride) range from 12-14 seconds.

| Rinse Conditioner (Wet Comb Out Test) | |
| --- | --- |
| Product | Time in Seconds |
| Example # 28 | 8 |
| Example # 33 | 10 |
| Stearyldimethylbenzyl ammonium chloride | 12 |

As can be seen, the compounds of the invention give significant conditioning properties to hair, and coupled with their mild nature with regard to skin and eyes, makes it a prime candidate for cosmetic applications.

Shampoo Formulation

The compounds of the present invention were also added to a simple shampoo formulation to show the potential for conditioning.

|  | Control | A | B |
| --- | --- | --- | --- |
| Sodium Laureth Sulfate (30% Active) | 50.0 | 50.0 | 50.0 |
| Cocamide DEA | 3.0 | 3.0 | 3.0 |
| Sodium Chloride | 2.0 | 2.0 | 2.0 |
| Cocamidopropyl betaine (35% Active) | 2.0 | — | — |
| Example # 27 | — | 0.5 | — |
| Example # 34 | — | — | 0.5 |
| Water | Quantity Sufficient to 100% | | |
| Total | 100.0 | 100.0 | 100.0 |

The above formulations were evaluated for softening properties and rated on a scale of 1-5. 5 being harshest.

| Softness Ratings | Rating |
| --- | --- |
| Control Formulation | 5 |
| Formulation A | 2 |
| Formulation B | 1 |

As the data clearly shows the compounds of the present invention are good conditioners and softeners when applied to the hair.

What is claimed:

1. A silicone compound which conforms to the following structure;

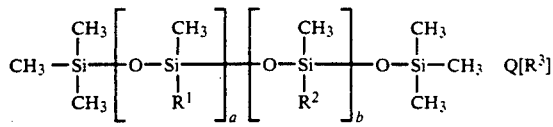

a is an integer from 1 to 200;
b is an integer from 1 to 50;
$R^1$ is selected from $—(CH_2)_nCH_3$ and phenyl;
n is an integer from 0 to 10;
$R^2$ is selected from;
  $—(CH_2)_3—(OCH_2CH_2)_x—(OCH_2CH(CH_3))_y—(OCH_2CH_2)_z—NH_3$; or
  $—(CH_2)_3—(CH_2)_v—N(H)_2—[(CH_2)_3—N(H)_2]_m—H$;
v is an integer ranging from 0 to 5;
x, y and z are integers and are independently selected from 0 to 20, with the proviso that the value of x+y+z ranges from 15 to 60;
m is an integer from 1 to 10;
$R^3$ is the anion of a fatty carboxylic acid and conforms to the following structure;

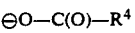

$R^4$ is alkyl having from 5 to 45 carbon atoms or mixtures thereof;
Q is an integer needed for charge balance and is equal to the number of nitrogen atoms present in the $R^2$ group.

2. A compound of claim 1 wherein
$R^2$ is $—(CH_2)_3—(OCH_2CH_2)_x—(OCH_2CH(CH_3))_y—(OCH_2CH_2)_z—NH_3$.

3. A compound of claim 2 wherein
$R^1$ is $CH_3$; a is 150; b is 4; x is 5; y is 5 and z is 5.

4. A compound of claim 2 wherein
$R^1$ is $CH_3$; a is 100; b is 2; x is 0; y is 10; and z is 5.

5. A compound of claim 2 wherein
$R^1$ is $CH_2CH_3$; a is 50; b is 1; x is 20; y is 20; and z is 20.

6. A compound of claim 1 wherein
$R^2$ is $—(CH_2)_3—(CH_2)_v—N(H)_2—[(CH_2)_3—N(H)_2]_m—H$;
m is an integer ranging from 1 to 10;
v is an integer ranging from 0 to 5.

7. A compound of claim 6 wherein;
$R^1$ is $CH_3$; a is 175; b is 10; w is 0; m is 1.

8. A compound of claim 6 wherein;
$R^1$ is $CH_3$; a is 200; b is 10; m is 1.

9. A compound of claim 6 wherein;
$R^1$ is $CH_3$; a is 50; b is 10; m is 5.

10. A compound of claim 1 wherein
$R^2$ is $—(CH_2)_3—(CH_2)_v—N(H)_2—[(CH_2)_3—N(H)_2]_m—H$;
v is 0; m is 1.

* * * * *